(12) United States Patent
Kitahara et al.

(10) Patent No.: US 6,194,603 B1
(45) Date of Patent: Feb. 27, 2001

(54) POLYISOCYANATE COMPOUND, PROCESS FOR PRODUCING THE SAME AND OPTICAL MATERIALS USING THE SAME

(75) Inventors: Yoshitaka Kitahara; Jian Jiang, both of Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 09/362,094

(22) Filed: Jul. 28, 1999

(30) Foreign Application Priority Data

Jul. 28, 1998 (JP) .................................................. 10-212991
Jul. 28, 1998 (JP) .................................................. 10-212992

(51) Int. Cl.[7] .................................................. C07C 249/00
(52) U.S. Cl. .......................................... 560/357; 351/159
(58) Field of Search ............................. 560/357; 351/159

(56) References Cited

U.S. PATENT DOCUMENTS

| | | | |
|---|---|---|---|
| 4,689,387 | * 8/1987 | Kajimoto et al. | ........................ 528/76 |
| 5,756,766 | * 5/1998 | Kawauchi et al. | ..................... 549/22 |

FOREIGN PATENT DOCUMENTS

| | | |
|---|---|---|
| 63-46213 | 2/1988 | (JP) . |
| 1-295201 | 11/1989 | (JP) . |
| 1-295202 | 11/1989 | (JP) . |
| 2-802 | 1/1990 | (JP) . |
| 2-153302 | 6/1990 | (JP) . |
| 4-159275 | 6/1992 | (JP) . |
| 5-105677 | 4/1993 | (JP) . |
| 06065193 | 3/1994 | (JP) . |
| 08208801 | 8/1996 | (JP) . |
| 08269161 | 10/1996 | (JP) . |
| 08291210 | 11/1996 | (JP) . |
| 08291211 | 11/1996 | (JP) . |
| 09001565 | 1/1997 | (JP) . |
| 9-052931 | 2/1997 | (JP) . |
| 09071631 | 3/1997 | (JP) . |
| 09071632 | 3/1997 | (JP) . |
| 10045707 | 2/1998 | (JP) . |
| 10245429 | 9/1998 | (JP) . |

* cited by examiner

*Primary Examiner*—Paul J. Killos
*Assistant Examiner*—Taylor V Oh
(74) *Attorney, Agent, or Firm*—Griffin & Szipl, P.C.

(57) ABSTRACT

A novel polyisocyanate compound, which compound is useful as a starting material for an optical material having excellent optical characteristics such as a high refractive index and a low dispersion, and a process for producing this compound at good efficiency. Specifically, a polyisocyanate compound represented by general formula (I):

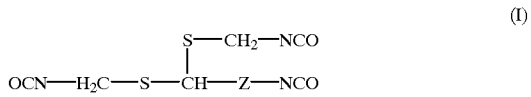

wherein Z represents a direct bond, or $-CH_2-$. The invention also relates to processes for producing the desired polyisocyanate compound through a tricarboxylic acid ester and a tricarbonyl hydrazide using a dihalogeno-aliphatic carboxylic acid lower alkyl ester and a thioglycolic acid lower alkyl ester. In addition, the invention relates to optical materials, such as lenses, etc., made by a polyaddition reaction of compounds of formula (I) and other monomers.

20 Claims, 2 Drawing Sheets

POLYISOCYANATE COMPOUND, PROCESS FOR PRODUCING THE SAME AND OPTICAL MATERIALS USING THE SAME

BACKGROUND OF THE INVENTION (a) Technical Field

The present invention relates to a polyisocyanate compound and a process for producing the same. More specifically, the present invention relates to a novel polyisocyanate compound useful as a starting material for an optical material which has excellent optical characteristics such as a high refractive index and low dispersion, and a process for producing the same with good efficiency.

Moreover the present invention relates to an optical material and an optical product using the same. More specifically, it relates to an optical material which has excellent optical characteristics such as high refractive index, low dispersion, excellent transparency, lack of optical distortion and the like, and which is also good in heat resistance, solvent resistance and weatherability, and to an optical product formed of this optical material, such as a lens, a prism, optical fibers, a substrate for a recording medium, a filter, a glass, a vase and the like.

(b) Related Art

In comparison with glass, plastics are lightweight, hard to break, and easy to dye. Therefore, plastics have been applied, in recent years, to optical use in various lenses and the like. As optical plastic materials, polyethylene glycol bisallyl carbonate (CR-39) and polymethyl methacrylate (PMMA) have been generally used. However, these plastic materials have a refractive index of 1.50 or less. Therefore, when they are used as lens materials, for example, the thickness of the lenses has to be increased with increasing lens power. Consequently, not only is the superiority of plastics lightweight materials impaired, but thick lenses have undesirable aesthetic properties. Furthermore, concave lenses in particular have been problematic in that the thickness (edge thickness) of the surrounding portion of the lens is increased and birefringence or chromatic aberration is liable to occur.

Therefore, in order to be able to decrease the thickness of the lens, while making the most of the characteristics of plastics with low specific gravity, a plastic material having a high refractive index has been in demand. Among materials having such performance are, for example, (1) a polymer comprising a xylylene diisocyanate compound and a polythiol compound (Japanese Unexamined Patent Publication JP-A-63-46213), (2) a resin comprising an aliphatic linear sulfur-containing difunctional isocyanate and a polythiol compound (Japanese Unexamined Patent Publication JP-A-2-153302), (3) a polymer comprising an aliphatic branched sulfur-containing difunctional isocyanate compound and a polythiol compound (Japanese Unexamined Patent Publication JP-A-10-45707).

Although the above-mentioned polymer (1) and resin (2) have an increased refractive index by limiting a combination with the polythiol compound to be polymerized, problems arise such as a decreased Abbe number and increased chromatic aberration in polymer (1) and decreased heat resistance in resin (2).

Meanwhile, the above-mentioned polymer (3) has a high refractive index, and improvements in the chromatic aberration and heat resistance are found therein, but the heat resistance is not yet satisfactory, and solvent resistance is also poor.

Furthermore, since these are uncrosslinked polymers obtained from difunctional isocyanate compounds, a special crosslinking agent is needed separately to improve the heat resistance and solvent resistance. Thus, there is a problem that it is unavoidable to limit the type of the polythiol compound to be polymerized.

It is therefore an object of the present invention to provide, under these circumstances, a novel polyisocyanate compound which can give an optical material having a high refractive index, low dispersion, excellent heat resistance and excellent solvent resistance. It is also an object and to provide a process for producing this compound at good efficiency.

It is a further object of the present invention to provide, under these circumstances, an optical material which has excellent optical characteristics such as high refractive index, low dispersion, excellent transparency, lack of optical distortion and the like, and which is also good in heat resistance, solvent resistance and weatherability. It is a still further object to provide an optical product formed of this optical material.

SUMMARY OF THE INVENTION

The present inventors have assiduously conducted investigations to achieve the above-mentioned objects, and have consequently found that a polyisocyanate compound having sulfur atoms contributing to a high refractive index and a low dispersion in a main skeleton and having three isocyanate groups as polymerization functional groups is a novel compound and is adapted to the above objects, and that this compound can be obtained at good efficiency by the specific processes described herein Moreover, the inventors have consequently found that an optical material formed of a poly(thio)urethane obtained by subjecting a component containing a specific polyisocyanate compound and a component containing a compound having two or more of hydroxyl groups, or mercapto groups, or both of these groups in a molecule, to a polyaddition reaction, can be adapted to the above objects.

These findings have led to the completion of the present invention.

That is, in accordance with the above objects, the present invention provides a polyisocyanate compound represented by general formula (I)

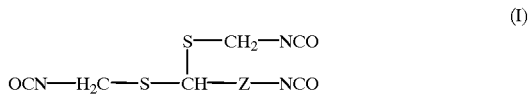

wherein Z represents a direct bond or —$CH_2$—.

Further, this polyisocyanate compound can be produced by the following processes (production processes 1 and 2) according to the present invention.

First, the production process 1 of the present invention is a process for producing a polyisocyanate compound represented by general formula (I-a)

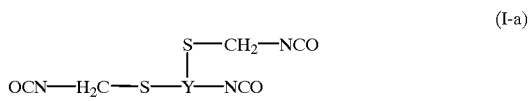

wherein Y represents =CH— or =$CHCH_2$—, comprising the steps of:

(a) reacting a dihalogeno-aliphatic carboxylic acid lower alkyl ester represented by general formula (II)

$$X_2-Y-COOR^1 \quad \ldots (II)$$

wherein X represents a halogen atom, Y is as defined above, and $R^1$ represents a lower alkyl group, with a thioglycolic acid lower alkyl ester to obtain a tricarboxylic acid ester represented by general formula (III)

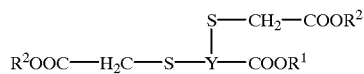

(III)

wherein $R^2$ represents a lower alkyl group, and Y and $R^1$ are as defined above;

(b) converting the tricarboxylic acid ester to a tricarbonyl hydrazide represented by general formula (IV)

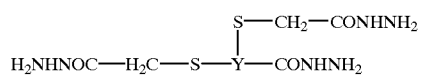

(IV)

wherein Y is as defined above; and (c) converting one or more of the carbonyl hydrazide groups of the general formula (IV) into an isocyanate group.

Next the production process 2 of the present invention is a process for producing 1,5-diisocyanato-3-isocyanatomethyl-2,4-dithiapentane represented by formula (I-b)

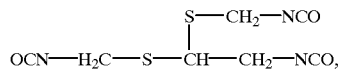

(I-b)

comprising the steps of:

(a) reacting a propiolic acid lower alkyl ester represented by general formula (V)

$$CH\equiv C-COOR^3 \quad \ldots (V)$$

wherein $R^3$ represents a lower alkyl group, with a thioglycolic acid lower alkyl ester, to obtain a tricarboxylic acid ester represented by general formula (VI)

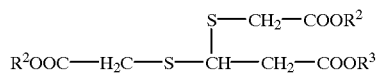

(VI)

wherein $R^2$ represents a lower alkyl group, and $R^3$ is as defined above;

(b) converting the tricarboxylic acid ester (VI) into 1,5-bis(hydrazinocarbonyl)-3-hydrazinocarbonylmethyl-2,4-dithiapentane represented by formula (VII),

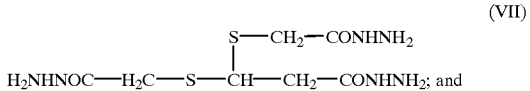

(VII)

(c) converting one or more of the carbonyl hydrazide groups into isocyanate groups.

Furthermore, the present invention provides an optical material formed of or comprising a poly(thio)urethane obtained by subjecting to a polyaddition reaction a monomer mixture comprising (A) a component containing at least a polyisocyanate compound represented by general formula (I)

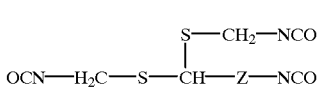

(I)

wherein Z represents a direct bond or —$CH_2$—, and (B) a component containing at least one member selected from the group consisting of (a) a compound having two or more mercapto groups in a molecule, (b) a compound having two or more hydroxyl groups in a molecule and (c) a compound having one or more hydroxyl groups and one or more mercapto groups in a molecule.

Furthermore, the present invention provides an optical product formed of or comprising the above-mentioned optical material.

Further objects, features and advantages of the present invention will become apparent with reference to the Detailed Description of the Preferred Embodiments, Examples and attached Drawings.

DETAILED DESCRIPTION OF THE PREFERRED EMBODIMENTS

Figure 1:
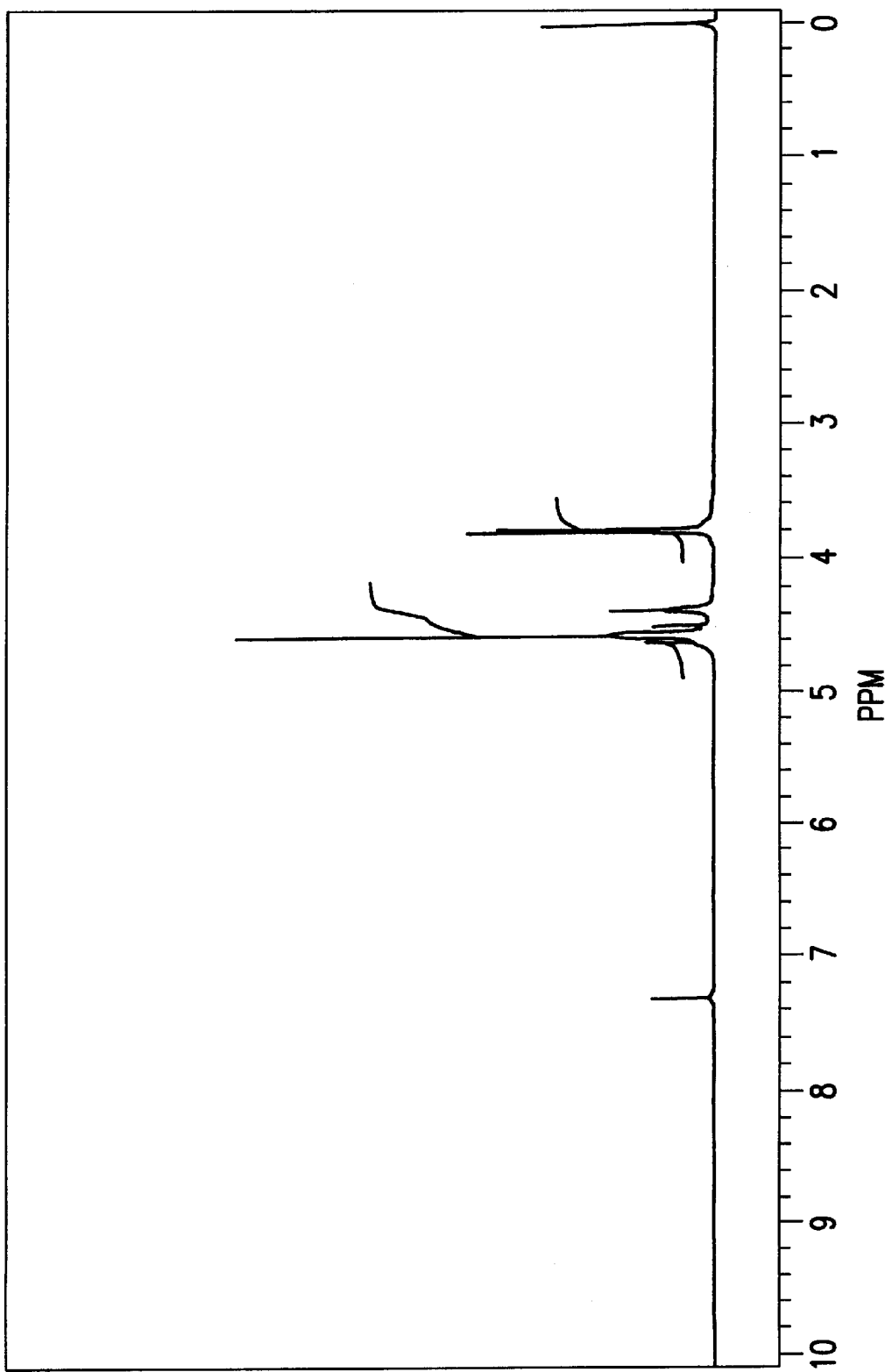
FIG. 1 is an $^1$H-NMR spectrum of 1,5-diisocyanato-3-isocyanatomethyl-2,4-dithiapentane obtained in Example 1.

The polyisocyanate compound of the present invention is a novel compound represented by general formula (I)

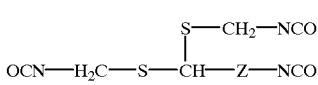

(I)

As is clear from general formula (I), this novel compound has a structure branched from the 3-position of a basic skeleton of a 2,4-dithiapentylene group, and has three isocyanate groups.

In general formula (I), Z is a direct bond or —$CH_2$—.

Since the polyisocyanate compound represented by general formula (I) contains sulfur atoms in its basic skeleton, the refractive index and the Abbe number of the polyisocyanate compound itself are increased. Accordingly, when an optical material is produced using this polyisocyanate compound, the refractive index and the Abbe number of the optical material are also increased. Furthermore, since this polyisocyanate compound has the three isocyanate groups, it itself becomes a crosslinking agent. Accordingly, when an optical material is produced using this polyisocyanate compound, high heat resistance, high solvent resistance and excellent mechanical properties can be imparted to the optical material without adding other crosslinking agents as secondary components.

As the polyisocyanate compound of the present invention represented by general formula (I), those having the following structures are specifically included.

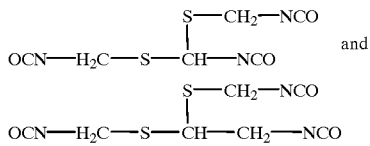
and

The process for producing this polyisocyanate compound represented by general formula (I) is not particularly limited. However, the compound of formula (I) can be produced at quite good efficiency according to the production processes 1 and 2, as described above.

Production process 1:

The production process 1 is a process for producing a polyisocyanate compound in which Z in general formula (I) is a direct bond or —$CH_2$—.

In this production process 1, a dihalogeno-aliphatic carboxylic acid lower alkyl ester represented by general formula (II)

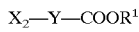 ... (II)

wherein X represents a halogen atom, Y represents =CH— or =CHCH$_2$— and $R^1$ represents a lower alkyl group,
is first reacted with a thioglycolic acid alkyl ester to form a tricarboxylic acid ester represented by general formula (III)

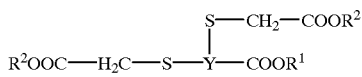

wherein $R^2$ represents a lower alkyl group, and Y and $R_1$ are as defined above.

In this reaction, it is preferable that 1 mol of the dihalogeno-aliphatic acid carboxylic acid lower alkyl ester represented by general formula (II) is reacted with substantially 2 mols of the thioglycolic acid lower alkyl ester in the presence of a hydrogen halide trapping agent. In this case, an appropriate solvent can be selected and used as required.

Next, the thus-obtained tricarboxylic acid ester represented by general formula (III) is reacted with hydrazine monohydrate, or the like, to convert the same to a tricarbonyl hydrazide represented by general formula (IV)

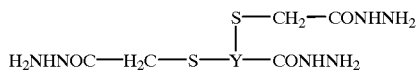

wherein Y is as defined above.

At this time, a solvent, such as a lower alcohol or the like, can be used as required.

Finally, the thus-obtained tricarbonyl hydrazide represented by general formula (IV) is reacted with nitrous acid in, for example, a hydrochloric acid aqueous solution, and a thermal rearrangement is conducted to convert the carbonyl hydrazide groups into isocyanate groups, whereby a desired polyisocyanate compound represented by general formula (I-a)

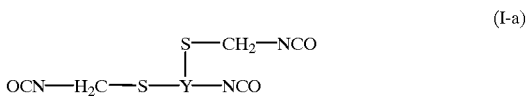

wherein Y is as defined above, is obtained.

Production process 2:

The production process 2 is a process for producing 1,5-diisocyanato-3-isocyanatomethyl-2,4-dithiapentane in which Z in general formula (I) is —$CH_2$—. Incidentally, this compound can also be produced by the above-mentioned production process 1.

In this production process 2, a propiolic acid lower alkyl ester represented by general formula (V)

 ... (V)

wherein $R^3$ represents a lower alkyl group, is first reacted with a thioglycolic acid lower alkyl ester to obtain a tricarboxylic acid ester represented by general formula (VI)

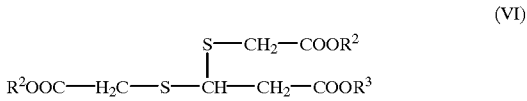

wherein $R^2$ represents a lower alkyl group, and $R^3$ is as defined above.

In this reaction, it is preferable that 1 mol of the propiolic acid lower alkyl ester represented by general formula (V) is reacted with substantially 2 mols of the thioglycolic acid lower alkyl ester in the presence of a radical or anionic catalyst, preferably an anionic quaternary ammonium salt. At this time, an appropriate solvent can be selected and used, as required.

Subsequently, the thus-obtained tricarboxylic acid ester represented by general formula (VI) is, as in the production process 1, reacted with hydrazine monohydrate to convert the same to 1,5-bis(hydrazinocarbonyl)-3-hydrazinocarbonylmethyl-2,4-dithiapentane represented by formula (VII)

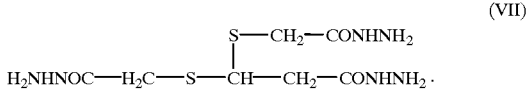

Finally, the carbonyl hydrazide groups of this 1,5-bis(hydrazinocarbonyl)-3-hydrazinocarbonylmethyl-2,4-dithiapentane are converted into isocyanate groups, as in the production process 1, to obtain the desired 1,5-diisocyanato-3-isocyanatomethyl-2,4-dithiapentane represented by formula (I-b)

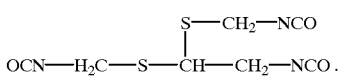

The lower alkyl group represented by $R^1$, $R^2$ and $R^3$ is preferably selected from a methyl group, an ethyl group, an n-propyl group, an isopropyl group or the like lower alkyl group.

Further, the polyisocyanate compound represented by general formula (I) can also be produced by a phosgene method in addition to the above-mentioned production processes of the present invention.

The phosgene method is next described by way of example. First, 1 mol of a dihalogenoacetonitrile represented by general formula (IX)

X₂CHCN   ... (IX)

wherein X represents a halogen atom, is reacted with substantially 2 mols of a thiocyanic acid salt represented by general formula (X)

MSCN   ... (X)

wherein M represents an alkali metal or ammonium, in the presence of a hydrogen halide trapping agent, to obtain dithiocyanatoacetonitrile represented by formula (XI)

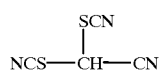

(XI)

Then, this dithiocyanatoacetonitrile (XI) is subjected to hydrogenation to convert the same to 1,5-diamino-3-aminomethyl-2,4-dithiapentane represented by formula (XII)

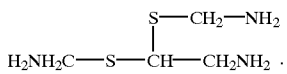

(XII)

Then, the compound of formula (XII) is reacted with phosgene to obtain the desired 1,5-diisocyanato-3-isocyanatomethyl-2,4-dithiapentane represented by formula The optical material of the present invention is formed of or comprises a poly(thio)urethane. As the component(A), one of the starting materials of the poly(thio)urethane, a component containing a polyisocyanate compound represented by general formula (I) as defined above is preferably used.

According to a further embodiment, the component (A) preferably contains, to appropriately improve properties, and the like, of the optical material, one or two or more types of a compound having two or more isocyanate groups in a molecule, in addition to the polyisocyanate compound represented by the above-mentioned general formula (I). Specific examples of these compounds include o-xylylene diisocyanate, m-xylylene diisocyanate, p-xylylene diisocyanate, α,α, α', α'-tetramethyl-p-xylylene diisocyanate, α,α,α',α'-tetramethyl-m-xylylene diisocyanate, 1,3,5-tris(isocyanatomethyl)benzene, hexamethylene diisocyanate, 1,4-diisocyanatobutane, isophorone diisocyanate, norbornene diisocyanate, bis(4,4'-isocyanatocyclohexyl)methane, 1,3-bis(isocyanatomethyl)cyclohexane, 1,3,5-tris(isocyanatomethyl)cyclohexane, 1,4-diisocyanatocyclohexane, 1,3,5-triisocyanatocyclohexane, lysine triisocyanate, 2,5-bis(isocyanatomethyl)-1,4-dithian, 1,3-dithiolan-4,5-diisocyanate, 4,5-bis(isocyanatomethyl)-1,3-dithiolan, isocyanatomethyl sulfide, 2-isocyanatoethyl sulfide, bis(isocyanatomethylthio)methane, 1,2-bis(isocyanatomethylthio)ethane, bis(2-isocyanatoethylthio) methane, 1,2-bis(2-isocyanatoethylthio)ethane, 1,7-diisocyanato-2,4,6-trithiaheptane, 1,5-diisocyanato-2-isocyanatomethyl-3-thiapentane, 1,4-diisocyanato-2-isocyanatomethyl-3-thiabutane, and the like including equivalents of the above.

The content of the polyisocyanate compound represented by general formula (I) in the component (A) is preferably 0.1 mol % or more, especially preferably 5 mol % or more.

As the component (B), another starting material of the poly(thio)urethane is preferably a component containing at least one member selected from the group consisting of (a) a compound having two or more mercapto groups in a molecule, (b) a compound having two or more hydroxyl groups in a molecule and (c) a compound having one or more hydroxyl groups and one or more mercapto groups in a molecule.

Examples of the compound having two or more mercapto groups in a molecule as the component (a) include 2,5-bis(mercaptomethyl)-1,4-dithian, 2,5-bis(mercaptomethyl)-1,4-dithian dimer and polymer (trimer or higher polymer), 1,2,3-trimercaptopropane, tetrakis(7-mercapto-2,5-dithiaheptyl)methane, 1,2-ethanedithiol, 1,3-propanedithiol, tetrakismercaptomethylmethane, 2-mercaptoethyl sulfide, pentaerythritol tetrakismercaptopropionate, pentaerythritol tetrakismercaptoacetate, 1,2-benzenedithiol, 1,3-benzenedithiol, 1,4-benzenedithiol, 1,3,5-benzenetrithiol, 1,2-dimercaptomethylbenzene, 1,3-dimercaptomethylbenzene, 1,4-dimercaptomethylbenzene, 1,3,5-trimercaptomethylbenzene, toluene-3,4-dithiol, tris(3-mercaptopropyl) isocyanurate, 1,3-bis(mercaptomethyl) cyclohexane, 1,4-bis(mercaptomethyl)cyclohexane, 2,2-bis(mercaptomethyl)-1,3-propanedithiol, 1,2-bis(2-mercaptoethylthio)-3-mercaptopropane, 4,8-bis(mercaptomethyl)-3,6,9-trithia-1,11-undecanedithiol, and the like including equivalents.

Further, examples of the compound having two or more hydroxyl groups in a molecule as the component (b) include ethylene glycol, trimethylolpropane, glycerin, dihydroxybenzene, catechol, 4,4'-dihydroxyphenyl sulfide, 2-hydroxyethyl sulfide, bisphenol A-propylene oxide 5-mol adduct, glycerin-propylene oxide 3-mol adduct, and the like, including equivalents.

In addition, examples of the compound having one or more hydroxyl groups and one or more mercapto groups in a molecule as the component (c) include 2-mercaptoethanol, 2,3-dimercaptopropanol, 1,2-dihydroxy-3-mercaptopropane, 4-mercaptophenol, and the like, including equivalents.

Component (B) is preferably the mercapto group-containing compound (a). Especially preferred are 2,5-bis(mercaptomethyl)-1,4-dithian represented by general formula (VIII)

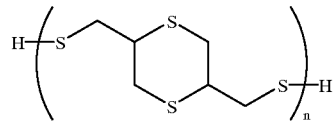

wherein n is an integer of from 1 to 20, and oligomers thereof.

With respect to the ratio of the component (A) to the component (B) in the present invention, it is preferable that the molar ratio of the isocyanate group in the component (A) to the total amount of the mercapto group and the hydroxyl group in the component (B), NCO group/(SH group+OH group), is in the range of from about 0.95 to about 1.05.

The monomer mixture containing component (A) and component (B) may additionally contain one or two or more types of the compound having two or more vinyl groups in the molecule to appropriately improve the properties, and the like, of the optical material, in addition to the components (A) and (B). With respect to the ratio of these compounds used, it is preferable that the (isocyanate group+ vinyl group)/(mercapto group+hydroxyl group) molar ratio be in the range of from about 0.95 to about 1.5 and the (vinyl group)/(isocyanate group) molar ratio be about 0.7 or less, and that polymerizable functional groups contained in the component (B) are all mercapto groups. Specific examples of these compounds include 2,5-bis(2-thia-3-butenyl)-1,4-dithian, divinylbenzene, ethylene glycol di(meth)acrylate, polyethylene glycol di(meth)acrylate, a urethane-modified (meth)acrylate containing at least two (meth)acryloxy groups in a molecule, and the like including equivalent compounds. The above-described (meth)acrylate includes both an acrylate and a methacrylate, and the (meth)acryloxy group includes both an acryloxy group and a methacryloxy group.

To the optical material of the present invention can be added an ultraviolet absorber, a coloring, a pigment, and the like, for improving light absorption characteristics, an antioxidant, a coloration inhibitor, and the like, for improving weatherability, and a release agent, and the like, for improving a moldability, as required.

Examples of the ultraviolet absorber include those of the benzotriazole type, benzophenone type, salicylic acid type, and the like, including equivalents thereof. Examples of the coloring and the pigment include those of the anthraquinone type, azo type and the like including equivalents thereof.

Examples of the antioxidant and the coloration inhibitor include those of the monophenol type, bisphenol type, high-molecular phenol type, sulfur type, phosphorus type, and the like, including equivalents. Examples of the release agent include a fluorine-type surfactant, a silicone-type surfactant, an acidic phosphate, a higher fatty acid, and the like, including equivalents.

Furthermore, a catalyst may be used, as required, to improve polymerization reactivity, and an amine compound, an organic metal compound, and the like, are effective. Specific examples of catalysts include triethylenediamine, hexamethylenetetramine, N,N-dimethyloctylamine, N,N,N', N'-tetramethyl-1,6-diaminohexane, 4,4'-trimethylenebis(1-methylpiperidine), 1,8-diazabicyclo-(5,4,0)-7-undecene, dimethyltin dichloride, dimethyltin bis(isooctylthioglycolate), dibutyltin dichloride, dibutyltin dilaurate, dibutyltin maleate, dibutyltin maleate polymer, dibutyltin diricinoleate, dibutyltin bis(dodecylmercaptide), dibutyltin bis(isooctylthioglycolate), dioctyltin dichloride, dioctyltin maleate, dioctyltin maleate polymer, dioctyltin bis(butylmaleate), dioctyltin dilaurate, dioctyltin diricinoleate, dioctyltin dioleate, dioctyltin di(6-hydroxy) caproate, dioctyltin bis(isooctylthioglycokate), didodecyltin diricinoleate, copper oleate, copper acetylacetonate, iron acetylacetonate, iron naphthenate, iron lactate, iron citrate, iron gluconate, potassium octanate, 2-ethylhexyl titanate, and the like including equivalents. The above-mentioned catalysts are equivalents. The above-mentioned catalysts are effectively used either singly or in combination of two or more types.

In addition, when a vinyl compound is contained in the monomer mixture, the use of an organic peroxide, an azo compound, or the like, other than the above-mentioned catalyst, is effective.

For example, the production of the optical material of the present invention using the polyisocyanate compound of the present invention is mentioned as follows. The uniform mixture of the component (A), the component (B), the additives and the catalyst is subjected to a known cast polymerization method, that is, it is cast into a die which is a combination of a glass or metal mold and a gasket made of a resin, and cured by heating. At this time, in order to expedite withdrawal of the resin after molding, the mold may previously be subjected to release treatment, or a release agent may be added to the mixture of the component (A), the component (B) and the like. The polymerization temperature varies depending on the compound used. The temperature is usually between about −20 and about +150° C. The polymerization time is between about 0.5 and about 72 hours. The optical material of the present invention can easily be dyed in water or an organic solvent using an ordinary disperse dye. In order to further expedite the dyeing, a carrier may be added or heating may be conducted. The thus-obtained optical material is especially preferably used as a plastic lens, although its use is not limited to this application.

EXAMPLES

The present invention is next illustrated more specifically by referring to the following Examples. However, the present invention is not at all limited to these Examples.

The physical properties of the resulting polyisocyanate compounds and optical materials (polymers) were evaluated according to the following methods.

(1) $^1$H-NMR spectrum (proton nuclear magnetic resonance spectrum)

Measured using an FT-NMR Device Model EX 270 supplied by JEOL.

(2) IR spectrum (infrared absorption spectrum) Measured using a MAGNA-IR Spectrometer Model 560 supplied by Nicolet.

(3) Refractive index (nD) and Abbe number (VD) Measured at 20° C. using a precision refractometer Model KPR-200 supplied by Kalnew.

(4) Appearance Visually observed.

(5) Heat resistance

Dynamic viscoelasticity was measured with a static tension of 100 g and a frequency of 10 kHz by means of a dynamic viscoelasticity-measuring device supplied by Toyo Seiki Seisakusho. The heat resistance was evaluated in terms of a temperature of a decreasing point in a chart of a modulus of elasticity obtained at a rate of temperature rise of 2° C./min.

(6) Weatherability

A lens (optical product using an optical material) was mounted on a weather meter fitted with a sunshine carbon arc lamp. When 200 hours passed, the lens was taken out, and the color thereof was compared with that of the lens before the test. The weatherability was evaluated according to the following standard.

o: unchanged

Δ: slightly yellowed x: yellowed (7) Solvent resistance

A wiping test using acetone was conducted, and the solvent resistance was evaluated according to the following standard.

o: unchanged x: The surface is roughened or swollen.

(8) Optical distortion

Visually observed by the Schlieren method. The optical distortion was evaluated according to the following standard.

0: No distortion is observed.

x: Distortion is observed.

Example 1

Production of 1,5-diisocyanato-3-isocyanatomethyl-2,4-dithiapentane Ethyl propiolate (14.7 g, 0.15 mols) and 31.8 g (0.3 mols) of methyl thioglycolate were dissolved in 125 ml of benzene. Tetrabutylammonium fluoride (0.78 g, 0.003 mols) was added as a catalyst in an ice bath, and the solution was then stirred at room temperature for 70 hours. Subsequently, the reaction solution was washed with a dilute sodium hydroxide aqueous solution and with water in that order, and dried. Benzene was distilled off under reduced pressure, and the residue was distilled under reduced pressure to obtain 31.1 g (0.10 mols) of 1,5-bis(methyloxycarbonyl)-3-ethyloxycarbonylmethyl-2,4-dithiapentane (boiling point: 127 to 129° C./0.02 mmHg).

This ester compound was dissolved in 30 ml of methanol, and added dropwise to a mixed solution of 45.0 g (0.90 mols) of hydrazine monohydrate and 170 ml of methanol at room temperature. After the completion of the dropwise addition, the mixture was stirred at 70° C. for 2 hours. After the mixture was allowed to cool, precipitated white crystals were collected through filtration, and recrystallized from methanol-water to obtain 22.0 g (0.075 mols) of 1,5-bis(hydrazinocarbonyl)-3-hydrazinocarbonylmethyl-2,4-dithiapentane.

Figure 2:
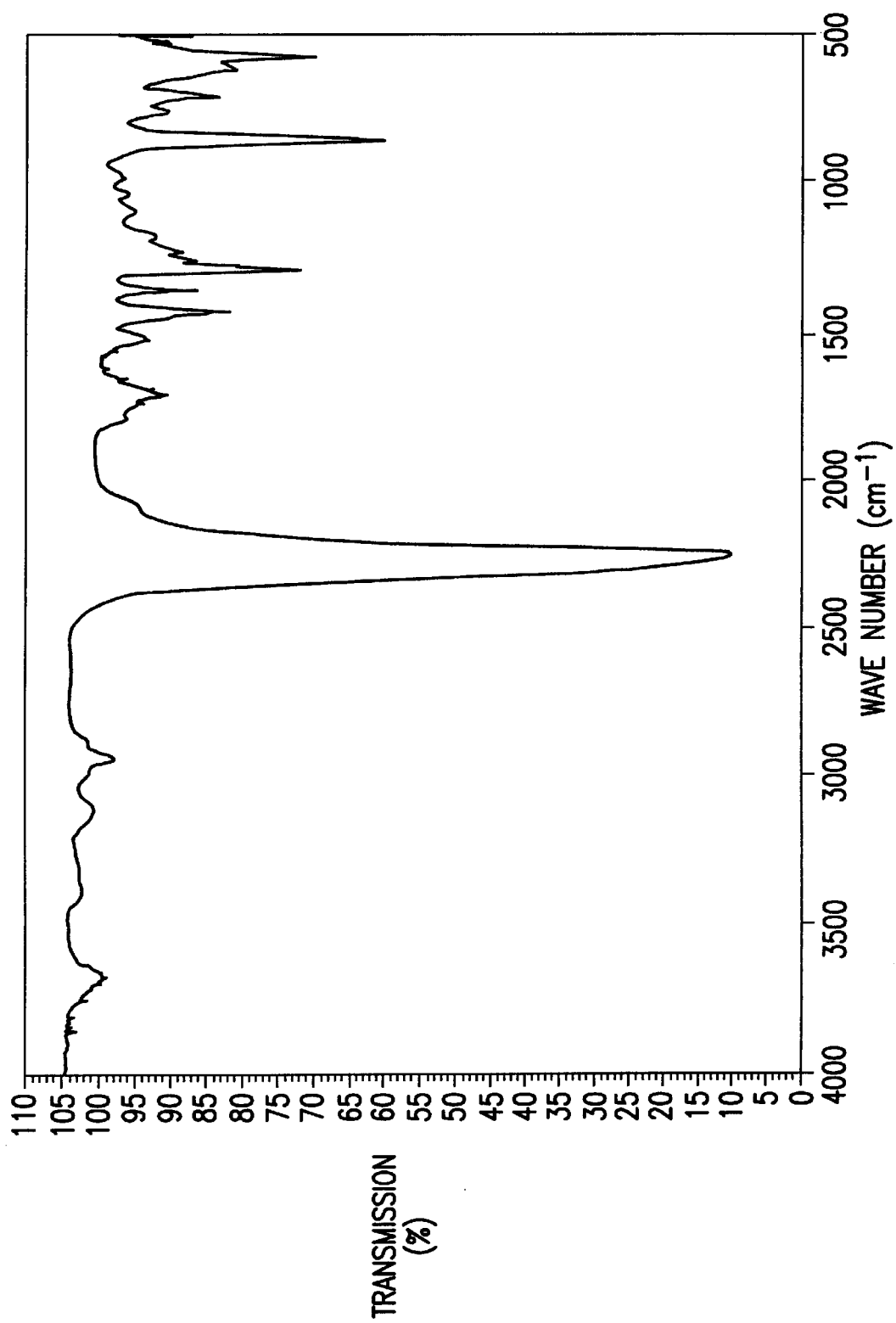
FIG. 2 is an IR spectrum of 1,5-diisocyanato-3-isocyanatomethyl-2,4-dithiapentane obtained in Example 1.

This hydrazide compound was dissolved in 160 g of a 7.2% by weight hydrochloric acid aqueous solution, and 16.6 g (0.24 mols) of sodium nitrite were added to a suspension of this in 150 ml of toluene. After the completion of the addition, the stirring was continued for 1 hour. The organic phase was withdrawn from the suspension, washed with water, dried (with magnesium sulfate), and then heated to complete the rearrangement reaction. Toluene as a solvent was fully removed from the reaction solution to obtain 11.1 g (0.045 mols) of a colorless transparent reaction product. This reaction product was identified to be a desired polyisocyanate compound from the $^1$H-NMR spectrum and the IR spectrum. The $^1$H-NMR spectrum of this novel polyisocyanate compound is shown in FIG. 1, and the IR spectrum thereof in FIG. 2.

Application Example 1

A mixture of 0.08 mols of 1,5-isocyanato-3-isocyanatomethyl-2,4-dithiapentane (designated DS-1 in Table 1) obtained in Example 1, 0.12 mols of 2,5-bis(mercaptomethyl)-1,4-dithian dimer (designated DBMD in Table 1) and $1.2 \times 10^{-4}$ mols of dibutyltin dilaurate (designated DBTDL in Table 1) was uniformly stirred, and cast into glass molds for forming a lens. The mixture was heat-polymerized at 50° C. for 10 hours, then at 60° C. for 5 hours and further at 120° C. for 3 hours to obtain a plastic lens. The properties of the resulting plastic lens are shown in Table 1. From Table 1, it is found that the polymer obtained by using the polyisocyanate compound of Example 1 is colorless and transparent, the refractive index (nD) is as high as 1.70, the Abbe number (VD) is also as high as 35 (low dispersion), the heat resistance (116° C.), the weatherability and the solvent resistance are excellent, and no optical distortion is observed.

Application Examples 2 to 4

The same procedure as in Application Example 1 was conducted except using a monomer composition containing the polyisocyanate compound DS-1 [1,5-diisocyanato-3-isocyanatomethyl-2,4-dithiapentane] obtained in Example 1 shown in Table 1 to obtain a plastic lens. The properties of these plastic lenses are shown in Table 1. From Table 1, it is found that the resulting plastic lenses are colorless and transparent, the refractive index (nD) is as high as between 1.65 and 1.69, the Abbe number (VD) is also as high as between 35 and 39 (low dispersion), the heat resistance (114 to 138° C.), the weatherability and the solvent resistance are all excellent, and no optical distortion is observed.

Application Comparative Example 1

A mixture of 0.06 mols of pentaerythritol tetrakismercaptopropionate (designated PETMP in Table 1), 0.12 mols of m-xylylene diisocyanate (designated XDI in Table 1) and $1.2 \times 10^{-4}$ mols of dibutyltin dilaurate (designated DBTDL in Table 1) was uniformly stirred, and cast into glass molds for forming a lens. The mixture was heat-polymerized at 50° C. for 10 hours, then at 60° C. for 5 hours and further at 120° C. for 3 hours to obtain a plastic lens. The properties of the resulting plastic lens are shown in Table 1. From Table 1, it is found that the plastic lens in Application Comparative Example 1 is colorless and transparent, no optical distortion is observed, and the solvent resistance is excellent, but the refractive index is as low as 1.59, and the heat resistance (86° C.) is also poor.

Application Comparative Examples 2 and 3

The same procedure as in Application Comparative Example 1 was conducted except using monomer compositions shown in Table 1 to obtain plastic lenses. The properties of these plastic lenses are shown in Table 1. From Table 1, it are found that the plastic lens in Application Comparative Example 2 has a high refractive index of 1.68 and is excellent in heat resistance (128° C.) and solvent resistance. However, it is colored yellow, Abbe number is low (25), the weatherability is poor, and optical distortion is observed. Furthermore, the plastic lens in Application Comparative Example 3 is colorless and transparent, the refractive index is as high as 1.68, and no optical distortion is observed. However, the Abbe number is low (29), and the heat resistance (89° C.) and the solvent resistance are also poor.

Since the novel polyisocyanate compound of the present invention has the aliphatic chain containing sulfur atoms as a basic skeleton, the refractive index and the Abbe number are high. It has three isocyanate groups, and is easily polymerized with at least one type of a compound having two or more hydroxyl groups in a molecule, a compound having two or more mercapto groups in a molecule and a compound having one or more hydroxyl groups and one or more mercapto groups in a molecule to provide a three-dimensionally crosslinked optical material. In addition, since the optical material obtained by using this polyisocyanate compound contains the sulfur atoms in the main chain and is further crosslinked, the refractive index and the Abbe number are high, the heat resistance, the weatherability, the solvent resistance and the transparency are excellent, and no optical distortion is observed. Accordingly, it is preferably used in optical products, for example, lenses such as spectacle lenses, camera lenses and the like, prisms, optical fibers, substrates for recording media used in optical disks, magnetic disks and the like, filters and the like. Furthermore, it is used in ornamental products such as a glass, a vase and the like which are obtained by making the most of the property of the high refractive index.

While the present invention has been illustrated by reference to certain Examples and Preferred Embodiments, one of ordinary skill in the art will recognize that modifications, improvements, additions, deletions, and substitutions to the Preferred Embodiments and Examples may be made without departing from the spirit and scope of the present invention, as defined by the appended claims.

TABLE 1

| | | Component (A) (mol) | Component (B) (mol) | Catalyst (mol) | $n_D/v_D$ | Appearance | Heat (° C.) Resistance | Weather-ability | Solvent Resistance | Optical Distortion |
|---|---|---|---|---|---|---|---|---|---|---|
| Application Example | 1 | DS-1 (0.08) | DBMD(0.12) | DBTDL $(1.2 \times 10^{-4})$ | 1.70/35 | colorless | 116 | ○ | ○ | ○ |
| | 2 | DS-1 (0.04) IMTM (0.06) | BMMD(0.12) | DBTDC $(1.2 \times 10^{-4})$ | 1.69/36 | colorless | 121 | ○ | ○ | ○ |
| | 3 | DS-1 (0.06) CHT1 (0.02) | DBMD(0.12) | DBTDL $(1.2 \times 10^{-4})$ | 1.69/36 | colorless | 124 | ○ | ○ | ○ |
| | 4 | DS-1 (0.08) | TMP (0.08) | DMTDC $(1.2 \times 10^{-4})$ | 1.67/36 | colorless | 138 | ○ | ○ | ○ |
| Application Comparative Example | 1 | XDI (0.12) | PETMP (0.06) | DBTDL $(1.2 \times 10^{-4})$ | 1.59/35 | colorless | 86 | Δ | ○ | ○ |
| | 2 | TDI (0.12) | XDT (0.07) PETMA (0.025) | DBTDL $(1.2 \times 10^{-4})$ | 1.68/25 | yellow | 128 | x | ○ | x |
| | 3 | TPDI (0.10) | XDT (0.10) | DBTDL $(1.0 \times 10^{-4})$ | 1.68/29 | colorless | 89 | Δ | x | ○ |

[Note 1]

DS-1: 1,5-diisocyanato-3-isocyanatomethyl-2,4-dithiapentane,
IMTM: bis(isocyanatomethylthio)methane,
CHTI: 1,3,5-triisocyanatocyclohexane,
DBMD: 2,5-bis(mercaptomethyl)-1,4-dithian dimer,
BMMD: 2,5-bis(mercaptomethyl)-1,4-dithian,
TMP: 1,2,3-trimercaptopropane,
DBTDL: di-n-butyltin dilaurate,
DMTDC: di-methyltin dichloride,
DBTDC: di-n-butyltin dichloride,
XDI: m-xylylene diisocyanate,
TDI: tolylene diisocyanate,
TPDI: 2,4-dithiapentane-1,3-diisocyanate
PETMP: pentaerythritol tetrakis(3-mercaptopropionate),
XDT: m-xylylene dithiol,
PETMA: pentaerythritol tetrakis(2-mercaptoacetate)

What is claimed is:

1. A polyisocyanate compound represented by general formula (I)

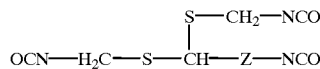

(I)

wherein Z represents a direct bond or —CH$_2$—.

2. A polyisocyanate compound according to claim 1, being 1,5-diisocyanato-3-isocyanatomethyl-2,4-dithiapentane.

3. A polyisocyanate compound according to claim 1, being 1,3,5-triisocyanato-2,4-dithiapentane.

4. A process for producing a polyisocyanate compound represented by general formula (I-a)

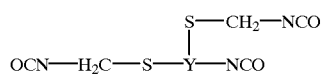

(I-a)

wherein Y represents =CH— or =CHCH$_2$—, comprising the steps of:

(a) reacting a dihalogeno-aliphatic carboxylic acid lower alkyl ester represented by general formula (II)

$$X_2—Y—COOR^1 \quad \ldots \text{(II)}$$

wherein X represents a halogen atom, Y is as defined above, and R$^1$ represents a lower alkyl group, with a thioglycolic acid lower alkyl ester to obtain a tricarboxylic acid ester represented by general formula (III)

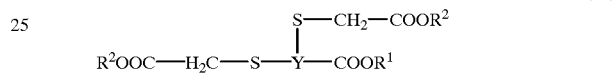

(III)

wherein R$^2$ represents a lower alkyl group, and Y and R$^1$ are as defined above;

(b) converting the tricarboxylic acid ester (III) into a tricarbonyl hydrazide represented by general formula (IV)

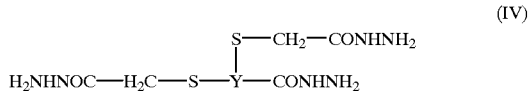

(IV)

wherein Y is as defined above; and (c) converting the carbonyl hydrazide groups of tricarbonyl hydrazide (IV) into isocyanate groups.

5. A process for producing 1,5-diisocyanato-3-isocyanatomethyl-2,4-dithiapentane represented by formula (I-b)

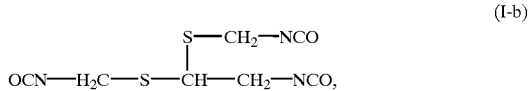

(I-b)

comprising the steps of:

(a) reacting a propiolic acid lower alkyl ester represented by general formula (V)

$$CH\equiv C—COOR^3 \quad \ldots \text{(V)}$$

wherein R$^3$ represents a lower alkyl group, with a thioglycolic acid lower alkyl ester to obtain a tricarboxylic acid ester represented by general formula (VI)

(VI)

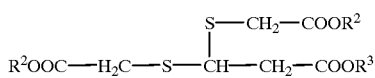

wherein $R^2$ represents a lower alkyl group, and $R^3$ is as defined above;

(b) converting the tricarboxylic acid ester (VI) into 1,5-bis(hydrazinocarbonyl)-3-hydrazinocarbonylmethyl-2,4-dithiapentane represented by formula (VII), (VII)

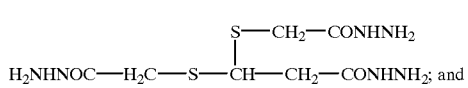

(c) converting the carbonyl hydrazide groups of compound (VII) into isocyanate groups.

6. An optical material comprising a poly(thio)urethane obtained by carrying out a polyaddition reaction on a monomer mixture comprising (A) a component containing at least a polyisocyanate compound represented by general formula (I)

(I)

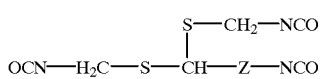

wherein Z represents a direct bond or —$CH_2$—, and (B) a component containing at least one member selected from the group consisting of (a) a compound having two or more mercapto groups in a molecule, (b) a compound having two or more hydroxyl groups in a molecule and (c) a compound having one or more hydroxyl groups and one or more mercapto groups in a molecule.

7. The optical material recited in claim 6, wherein component (B) comprises, as compound (a) a compound represented by general formula (VIII)

(VIII)

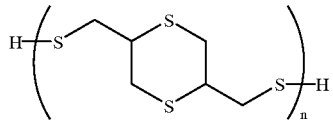

wherein n represents an integer of from 1 to 20.

8. A lens comprising the optical material of claim 6.

9. A lens according to claim 8, wherein component (A) comprises 1,5-diisocyanato-3-isocyanatomethyl-2,4-dithiapentane.

10. A lens according to claim 9, wherein component (B) comprises pentaerythritol tetrakismercapto propionate.

11. A lens according to claim 10, wherein component (B) further comprises m-xylylene diisocyanate.

12. A lens according to claim 8, wherein component (A) comprises 1, 3,5-triisocyanato-2,4-dithiapentane.

13. A lens according to claim 12, wherein component (B) comprises pentaerythritol tetrakismercapto propionate.

14. A lens according to claim 13, wherein component (B) further comprises m-xylylene diisocyanate.

15. A lens according to claim 8, made by cast polymerization.

16. A lens according to claim 9, made by cast polymerization.

17. A lens according to claim 11, made by cast polymerization.

18. A lens according to claim 12, made by cast polymerization.

19. A lens comprising the optical material of claim 7.

20. A lens according to claim 16 made by cast polymerization.

\* \* \* \* \*